(12) United States Patent
El-Haddad (10) Patent No.: US 10,492,999 B2
(45) Date of Patent: Dec. 3, 2019

(54) LOCKING BRAKES FOR ENTERAL FEEDING TUBE RETENTION MEMBER

(71) Applicant: H. Lee Moffitt Cancer Center and Research Institute, Inc., Tampa, FL (US)

(72) Inventor: Ghassan Elias El-Haddad, Tampa, FL (US)

(73) Assignee: H. Lee Moffitt Cancer Center and Research Institute, Inc., Tampa, FL (US)

( * ) Notice: Subject to any disclaimer, the term of this patent is extended or adjusted under 35 U.S.C. 154(b) by 209 days.

(21) Appl. No.: 15/195,419

(22) Filed: Jun. 28, 2016

(65) Prior Publication Data

US 2016/0302999 A1   Oct. 20, 2016

Related U.S. Application Data

(63) Continuation of application No. PCT/US2014/072469, filed on Dec. 29, 2014.
(Continued)

(51) Int. Cl.
*A61J 15/00*     (2006.01)
*A61M 25/02*    (2006.01)

(52) U.S. Cl.
CPC ....... *A61J 15/0042* (2013.01); *A61J 15/0015* (2013.01); *A61J 15/0023* (2013.01);
(Continued)

(58) Field of Classification Search
CPC . A61J 15/0034; A61J 15/0061; A61J 15/0065
See application file for complete search history.

(56) References Cited

U.S. PATENT DOCUMENTS

| | | | | |
|---|---|---|---|---|
| 559,620 A | * | 5/1896 | Shearer | A61M 3/0283 604/40 |
| 3,253,594 A | * | 5/1966 | Matthews | A61M 25/1009 604/103.03 |

(Continued)

OTHER PUBLICATIONS

Foutch et al., A Critical Analysis of the Sacks-Vine Gastrostomy Tube: A Review of 120 Consecutive Procedures, 1988, The American Journal of Gastroenterology, vol. 83, No. 8, pp. 812-815.
(Continued)

*Primary Examiner* — Bhisma Mehta
*Assistant Examiner* — Matthew A Engel
(74) *Attorney, Agent, or Firm* — Nicholas Pfeifer; Smith & Hopen, P.A.

(57) ABSTRACT

The present invention includes an indwelling tube having a plurality of projections extending outwardly from an exterior surface of the tube and a retention member designed to receive the tube. The retention member includes a projection passage to enable the retention member to receive and pass projections through the passage when the projection and passage are aligned so that the retention member can slide axially along the tube. When the projections and passage are out of alignment, the retention member can be secured between two projections. The present invention enables accurate placement of the retention member along the tube to aid in securing the tube at a desired depth in a patient's body. In a certain embodiment, the retention member may include a locking passage to receive and temporarily secure a projection to the retention member.

19 Claims, 5 Drawing Sheets

Related U.S. Application Data (60) Provisional application No. 62/047,367, filed on Sep. 8, 2014, provisional application No. 61/928,505, filed on Jan. 17, 2014, provisional application No. 61/921,766, filed on Dec. 30, 2013.

(52) U.S. Cl.
CPC ....... *A61J 15/0034* (2013.01); *A61J 15/0073* (2013.01); *A61M 25/02* (2013.01); *A61J 2200/70* (2013.01); *A61M 2025/0233* (2013.01)

(56) References Cited

U.S. PATENT DOCUMENTS

| | | | | |
|---|---|---|---|---|
| 3,372,443 | A * | 3/1968 | Daddona, Jr. | A41F 1/002 24/303 |
| 3,565,073 | A * | 2/1971 | Giesy | A61F 5/449 604/343 |
| 3,896,816 | A * | 7/1975 | Mattler | A61M 25/00 604/103.03 |
| 3,915,171 | A * | 10/1975 | Shermeta | A61J 15/0015 604/101.05 |
| 3,952,726 | A * | 4/1976 | Hennig | A61F 2/0018 128/DIG. 25 |
| 3,961,632 | A * | 6/1976 | Moossun | A61J 15/0015 128/DIG. 26 |
| 4,154,226 | A * | 5/1979 | Hennig | A61F 2/0018 128/DIG. 25 |
| 4,205,678 | A * | 6/1980 | Adair | A61F 5/448 604/343 |
| 4,258,705 | A * | 3/1981 | Sorensen | A61F 2/0018 600/30 |
| 4,338,937 | A * | 7/1982 | Lerman | A61F 2/0018 128/887 |
| 4,666,433 | A * | 5/1987 | Parks | A61J 15/0015 128/DIG. 12 |
| 4,863,438 | A * | 9/1989 | Gauderer | A61M 39/0247 604/105 |
| 4,921,484 | A * | 5/1990 | Hillstead | A61M 25/10 604/104 |
| 5,007,900 | A * | 4/1991 | Picha | A61J 15/0015 604/106 |
| 5,073,166 | A | 12/1991 | Parks et al. | |
| 5,080,650 | A | 1/1992 | Hirsch et al. | |
| 5,092,850 | A | 3/1992 | Buma | |
| 5,232,451 | A | 8/1993 | Freitas et al. | |
| 5,267,969 | A * | 12/1993 | Hirsch | A61J 15/0015 128/DIG. 26 |
| 5,306,226 | A * | 4/1994 | Salama | A61F 2/0009 128/DIG. 25 |
| 5,312,363 | A * | 5/1994 | Ryan | A61B 17/3496 137/846 |
| 5,391,159 | A * | 2/1995 | Hirsch | A61J 15/0019 604/175 |
| 5,431,662 | A * | 7/1995 | Nicholas | A61B 17/0218 606/119 |
| 5,484,420 | A | 1/1996 | Russo | |
| 5,910,128 | A | 6/1999 | Quinn | |
| 6,039,714 | A * | 3/2000 | Cracauer | A61J 15/0034 604/103.03 |
| 6,113,609 | A * | 9/2000 | Adams | A61B 17/0643 606/139 |
| 6,352,543 | B1 * | 3/2002 | Cole | A61B 17/0057 128/898 |
| 6,656,194 | B1 * | 12/2003 | Gannoe | A61F 5/0003 604/96.01 |
| 7,909,799 | B2 * | 3/2011 | Frassica | A61B 1/0008 604/165.04 |
| 8,029,522 | B2 * | 10/2011 | Ortiz | A61B 17/3421 606/153 |
| 8,057,429 | B2 * | 11/2011 | Nath | A61J 15/0015 604/97.02 |
| 8,932,263 | B2 * | 1/2015 | Rosenberg | A61M 5/158 604/174 |
| 2005/0177174 | A1 * | 8/2005 | Ginsberg | A61B 17/3403 606/108 |
| 2005/0283235 | A1 * | 12/2005 | Kugler | A61B 17/12009 623/14.13 |
| 2006/0041230 | A1 | 2/2006 | Davis | |
| 2006/0052752 | A1 * | 3/2006 | McMichael | A61J 15/0057 604/175 |
| 2006/0079845 | A1 * | 4/2006 | Howard | A61M 25/02 604/175 |
| 2007/0032807 | A1 * | 2/2007 | Ortiz | A61B 17/12 606/153 |
| 2007/0142780 | A1 * | 6/2007 | Van Lue | A61B 17/3462 604/167.01 |
| 2007/0156117 | A1 * | 7/2007 | Adams | A61J 15/0015 604/533 |
| 2007/0167923 | A1 * | 7/2007 | Deal | A61B 17/3415 604/270 |
| 2008/0082081 | A1 * | 4/2008 | Melsheimer | A61M 25/02 604/523 |
| 2008/0114384 | A1 * | 5/2008 | Chang | A61B 17/1114 606/153 |
| 2009/0299434 | A1 * | 12/2009 | Imran | A61B 5/4238 607/40 |
| 2009/0318854 | A1 * | 12/2009 | Bailey | A61M 39/0247 604/27 |
| 2009/0318873 | A1 * | 12/2009 | Bailey | A61M 39/0247 604/177 |
| 2011/0009828 | A1 | 1/2011 | Prechtel et al. | |
| 2011/0218388 | A1 * | 9/2011 | Ball | A61F 5/0079 600/30 |
| 2011/0288534 | A1 * | 11/2011 | Aguirre | A61J 15/0015 604/535 |
| 2012/0016298 | A1 * | 1/2012 | DeLegge | A61B 17/3415 604/96.01 |
| 2012/0238959 | A1 * | 9/2012 | Thorne | A61M 25/02 604/177 |
| 2014/0163529 | A1 * | 6/2014 | Karmazyn | A61J 15/0015 604/535 |

OTHER PUBLICATIONS

Rombeau et al., Atlas of Nutritional Support Techinques, Little, Brown and Company, 1989, pp. 132-136.

International Search Report for PCT/US2014/072469 with an International Filing date of Dec. 29, 2014, dated Apr. 29, 2015.

\* cited by examiner

LOCKING BRAKES FOR ENTERAL FEEDING TUBE RETENTION MEMBER

CROSS-REFERENCE TO RELATED APPLICATIONS

This nonprovisional application is a continuation of prior filed International Application, No. PCT/US2014/072469 filed on Dec. 29, 2014, which claims priority to provisional application No. 62/047,367, entitled "LOCKING BRAKES FOR ENTERAL FEEDING TUBE RETENTION MEMBER," filed Sep. 8, 2014, provisional application No. 61/928,505, entitled "LOCKING BRAKES FOR ENTERAL FEEDING TUBE RETENTION MEMBER," filed Jan. 17, 2014, and provisional application No. 61/921,766, entitled "LOCKING BRAKES FOR GASTROSTOMY EXTERNAL RETENTION DISC," filed Dec. 30, 2013 by the same inventor(s).

BACKGROUND OF THE INVENTION

1. Field of the Invention

This invention relates, generally, to indwelling medical devices. More specifically, it relates to an improvement in the tube and retention member coupling to maintain the external retention member's desired location along the tube.

2. Brief Description of the Prior Art

Percutaneous (placed through the skin) enteral feeding tubes are extremely prevalent in the medical field for providing patients who have a functioning gastrointestinal with a means for receiving nutrients when they are unable to eat through their mouths. Percutaneous enteral feeding tubes are used when normal oral intake of nutrients is insufficient (e.g., anorexia, burn victims, cystic fibrosis) and/or unsafe due to anatomic or neurologic dysfunction (e.g., cancer, stroke, head trauma, GI dysfunction/obstruction, neuromuscular disease, etc. . . . ). It is estimated that greater than 200,000 gastrostomy (stomach) tubes are placed each year in the US alone (See Roche V: *Percutaneous endoscopic gastrostomy. Clinical care of PEG tubes in older adults.* Geriatrics 2003; 58(11):22-26, 28-29.)

A common potential issue associated with percutaneous enteral feeding tubes is securing the tube in place. Accidental dislodgment is one of the most frequent causes of avoidable cost and consternation related to percutaneous enteral feeding tubes. For example, accidental gastrostomy dislodgement is an estimated $23 Million problem in the U.S. (See Rosenberger, L H, Newhook, T, Schirmer, B, et al: *Late accidental dislodgement of a percutaneous endoscopic gastrostomy tube: an underestimated burden on patients and the health care system.* Surg. Endosc. 25(10): p. 3307-11, 2011.) In order to prevent dislodgement, a combination of an external retention member or external bolster (i.e. a disc, or linear bolster) is often used to keep internally retained feeding tubes (by a balloon or bumper) in place. After placement of the percutaneous feeding tube, the internal retention device (i.e. balloon, or bumper) is pulled against the stomach wall, then the external retention member or external bolster is pushed down to the skin. The only thing that keeps the retention member or external bolster in place is friction around the tube. When the retention member or external bolster remains close to the skin, there is no significant motion of the internal balloon or bumper, and the risk of pericatheter leakage is decreased. When the retention member or external bolster slides back, the gastrostomy tube is no longer held in place and there is an increasing "back and forth" motion of the balloon. This "back and forth" motion leads to an increased risk of complications, including peritube leakage, skin excoriation, infection, bleeding, inadequate feeding, and tube replacement/upsizing. The enteral secretions leaking around the tube cause inflammation; skin excoriation; infection; widening of the tract, thereby causing more leakage ultimately leading to tube dislodgment; exchange/upsizing of the tube; possible need for antibiotic therapy; or even emergency department visits and hospital admissions. In addition, the forward dislodgement of the tube may lead to gastric or intestinal obstruction, with severe abdominal pain and inability to get needed nutrients.

Currently, the methods used to keep the retention member or external bolster in place, vary between addition of a plastic ring, tightening a 0-silk suture or tying a zip-tie around the neck of the retention member or external bolster. However, these methods restrict the lumen of the tube, which increases the risk of tube occlusion. The external retention mechanism for most percutaneous enteral feeding tubes, whether it is a gastrostomy (G) (tube in stomach), gastrojejunostomy (GJ) (tube in small bowel through stomach) or jejunostomy tube (J) (tube in small bowel) is a similar retention member that is pushed down to the skin, and has the same mechanism of action. Friction with the tube is the means by which the retention member is held in place.

Currently, the available designs and methods for securing the location of a retention member or external bolster at a desired location along an indwelling tube lack the ability to secure them in a simplistic manner without increasing the risk of tube occlusion. Available designs also secure the location of the retention member or external bolster to the tube through internal interaction with them.

U.S. Pat. No. 5,092,850 to Buma teaches a more complex design using saw teeth on both the tube and the retention member and a compression element to secure the location of the retention member. Essentially this is a screw like securing means, which can be more expensive to manufacture. The saw teeth design can also cause increased discomfort when contacting the patient's skin.

U.S. Pat. No. 5,484,420 to Russo teaches securing the location of a retention member along a tube using a twist lock or zip tie like fastening means. This design increases the risk of tube occlusion, which is a major problem with the current state of the art.

U.S. Pat Application No. 20040186461 to DiMatteo teaches a catheter with an adjustable cuff. The locatable cuff is adapted to mate with the external mounting projection on the tube, but the cuff is not capable of sliding along the tube to another projection. The cuff must be removed from the tube to be relocated and contains fastening means to secure both halves of the cuff around the projection.

Accordingly, what is needed is a simple indwelling tube and retention member design that prevents the retention member from being dislodged and moving to an undesirable location along the tube while also not increasing the risk of tube occlusion. However, in view of the art considered as a whole at the time the present invention was made, it was not obvious to those of ordinary skill in the field of this invention how the shortcomings of the prior art could be overcome.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for a simple indwelling tube and retention member design that prevents the retention member from being dislodged and moving to an undesirable location along the tube while also not increasing the risk of tube occlusion is now met by a new, useful, and nonobvious invention.

The novel structure includes a tube and a retention member or external bolster. The tube has a distal end and a proximal end, where the distal end is insertable into a body. The tube also contains a plurality of projections extending outward from the external surface of the tube. The projections are preferably aligned with one another along a longitudinal axis of the tube and are spaced equidistance from one another. The projections preferably extend outward a distance such that the tube remains capable of sliding inside a peel-away sheath if need be.

The retention member has a length extending axially, an outer perimeter, a central bore through the axial cross-section of the retention member, an inner diameter, an outer surface being perpendicular to the radial direction of the retention member, and inner surface being perpendicular to the radial direction of the retention member. The retention member is capable of receiving the tube through the central bore and the retention member's inner radius has a magnitude less than the sum of the magnitude of the extension of one projection and the magnitude of the radius of the tube's external surface.

A projection passage is disposed adjacent to the retention member's internal surface, and is of a size and shape such that the projections on the external surface of the tube can enter and pass through the passage when the passage and projections are aligned. The retention member also includes a buffering extension that could be cylindrical (most commonly) or rectangular prism, having the same internal diameter and projection passage as the retention member. The extension extends towards the proximal end of the tube in the axial direction of the retention member. The length of the extension in the axial direction is such that the sum of the length of the retention member and the length of the extension in the axial direction is slightly smaller than the distance between projections.

A certain embodiment may include a locking passage adapted to receive a projection, the locking passage having a shape such that the projection is incapable of leaving a securing end without being forced away from the body.

A certain embodiment may utilize a distance measuring system disposed on the external surface of the tube extending from the distal end tube to the proximal end of the tube.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

Figures 1, 2:
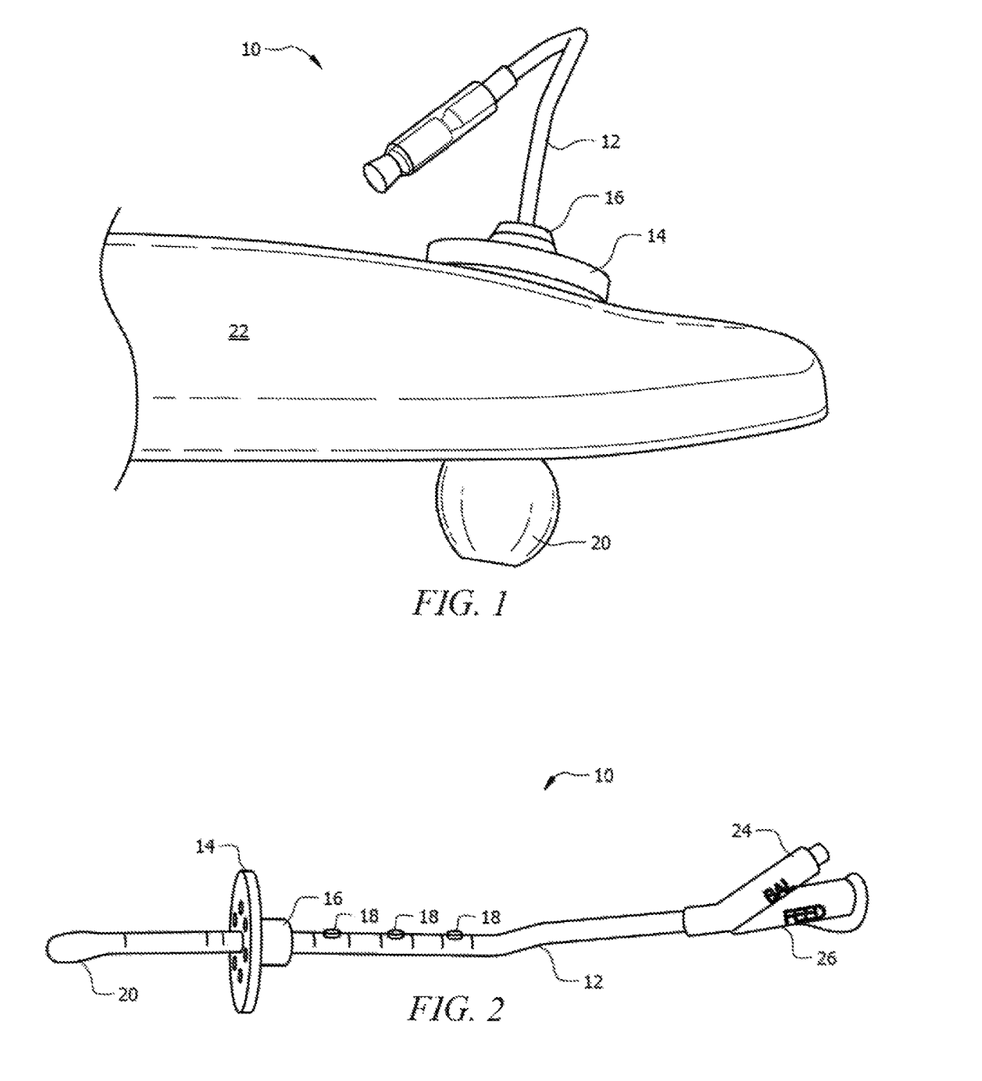
FIG. 1 is a perspective view of an indwelling enteral feeding tube inserted through an artificial abdominal wall with an external retention member secured to the tube at a location such that an internal retention member (i.e. inflatable retention balloon, or bumper) is an appropriate distance from the interior wall of the abdomen.
FIG. 2 is a perspective view of an embodiment of the present invention.

As shown in FIGS. 1 and 2, a certain embodiment of the present invention, generally denoted by reference numeral 10, includes an indwelling tube 12, having external projections 18 adapted to engage with retention member 14. Indwelling tube 12 includes an internal retention member such as an inflatable retention balloon or bumper 20 to further aid in retaining tube 12. Indwelling tube 12 is designed to pass through an opening in a body, such as abdominal wall 22 (abdominal wall 22 is an artificial abdominal wall to improve clarity), and remain secured in place by inflatable retention balloon or bumper 20 and external retention member 14. It should be noted that the type of indwelling tube illustrated is a G tube. However, alternate tubes such as GJ or J tubes have a catheter that extends beyond the balloon (or bumper) and the current invention is applicable to GJ and J tubes as well.

As shown in FIG. 2, indwelling tube 12 further includes feeding port 26 for providing nutrition to a patient and inflation port 24 for inflating balloon 20 (or in an alternate embodiment of the invention, the internal retentions means may be a bumper without the need for an inflation port). Indwelling tube 12 has a distal end containing inflatable balloon 20 and a proximal end containing feeding port 26 and balloon inflation port 24. External projections 18 are located between the proximal and distal ends on the external surface of tube 12, and extend outward in a radial direction from tube 12.

Figure 3:
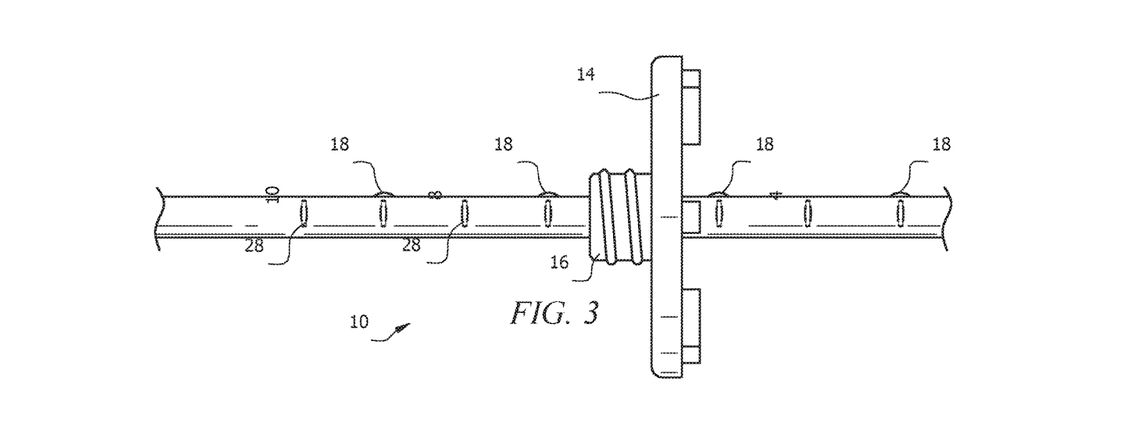
FIG. 3 is a close-up view of the interaction of the retention member and tube.

As shown in FIG. 3, projections 18 are longitudinally aligned, about tube 12, at an equidistance from one another. In a certain embodiment, projections 18 are spaced 1.5 cm from one another, however, any spacing between projections may be chosen by one of ordinary skill in the art. A certain embodiment may also include distance-measuring system 28 to provide a user with a scale for determining the depth of tube 12 when being placed inside the patient. Distance-measuring system 28 enables the user to secure the tube at a desired depth to improve the accuracy of insertion.

Projections 18 extend outward, at a predetermined magnitude, from the external surface of tube 12 in the radial direction. The predetermined magnitude is greater than the difference between the diameter of the external surface of tube 12 and the internal diameter of retention member 14 to prevent retention member 14 from sliding axially about tube 12.

Figure 4:
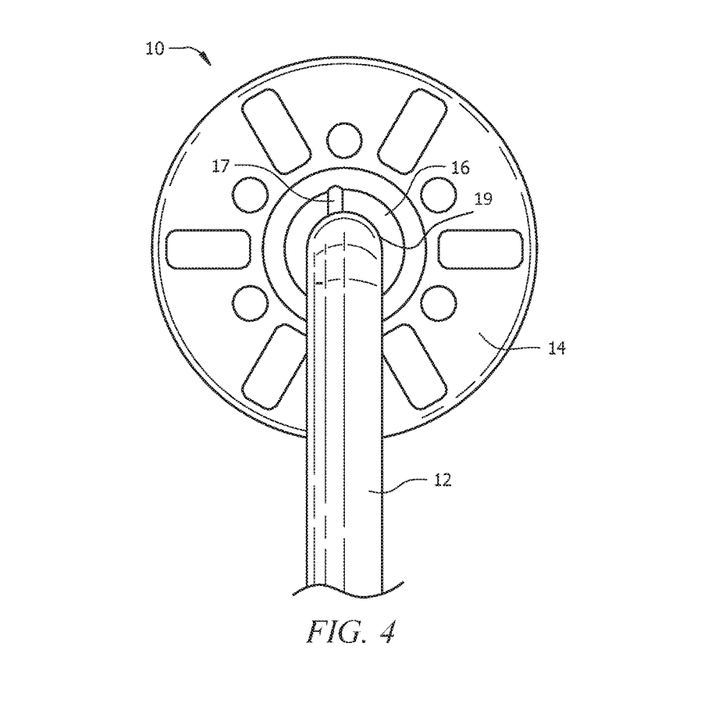
FIG. 4 is a close-up longitudinal perspective view of the interaction of the retention member and tube.

As shown in FIGS. 4 and 5, retention member 14 is preferably cylindrical (but may be of any predetermined geometrical configuration) with bore 19 through retention member 14, running parallel with the longitudinal axis of retention member 14, creating an inner diameter capable of receiving tube 12. Retention member 14 has an outer perimeter (or diameter when cylindrical) extending outward in the radial direction from the longitudinal axis and a length extending along the longitudinal direction. The outer perimeter extends outward a distance that is greater than the hole in the patient's body to prevent retention member 14 from entering the patient's body. In a certain embodiment, retention member 14 can have any shape so long as the outer perimeter extends outward far enough to prevent it from entering the patient's body.

Retention member 14 includes projection passage 17 extending the length of retention member 14. Projection passage 17 is adapted to receive projections 18 such that retention member 14 can slide longitudinally along tube 12 when passage 17 and projections 18 are aligned. Projections 18 secure retention member 14 between two projections when retention member 14 is rotated such that projections 18 and passage 17 are out of alignment.

Retention member 14 further includes buffering extension 16 extending from retention member 14. As shown in FIG. 3, buffering extension 16 has a predetermined length in the axial direction such that the total length of retention member 14 and buffering extension 16 fits snuggly between two projections 18 to prevent substantial "back and forth" movement of indwelling tube 12. Buffering extension 16 shares the same internal diameter and projection passage as retention member 14. Buffering extension 16 may have any shape so long as it can slide along tube 12 when passage 17 and projections 18 are aligned and can remain secured between two projections 18 when projections 18 and passage 17 are out of alignment.

As shown in FIG. 5, a certain embodiment of retention member 14 includes both projection passage 17 and locking passage 30. Locking passage 30 is preferably L-shaped as shown in FIGS. 5A and 5E and is preferably located on retention member 14 (specifically on extension 16) at a different site than projection passage 17. Additionally, locking passage 30 includes securing end 32 located at the end of the L-shape furthest from the entrance of locking passage 30. As shown in FIG. 5C, retention member 14 moves along tube 12 passing external projections 18 through projection passage 17 until retention member 14 has reached a desired location along tube 12. As shown in FIG. 5D, retention member 14 is then rotated with respect to tube 12 to align one of projections 18 with locking passage 30 as shown in FIG. 5E. One of projections 18 is then inserted into locking passage 30 and retention member 14 is rotated with respect to tube 12 to lock projection 18 in securing end 32, see FIG. 5F.

Figure 5A:
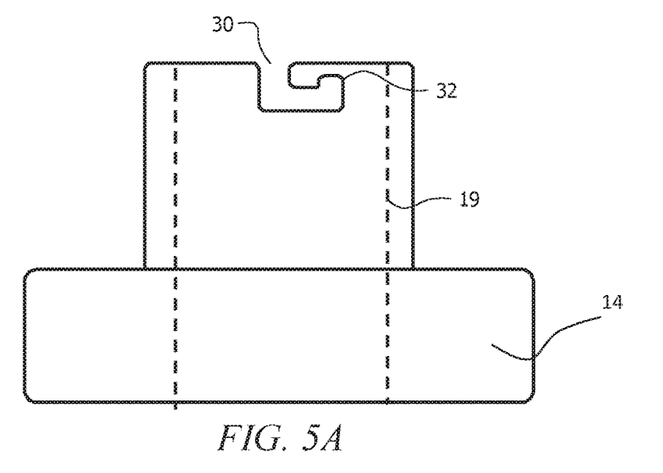
FIG. 5A is a certain embodiment of the retention member having a locking mechanism.
Figure 5B:
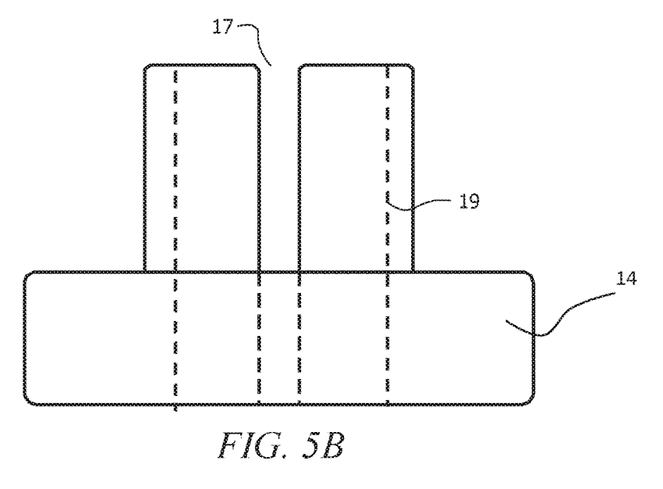
FIG. 5B is a side view of FIG. 5A showing the projection passage.
Figure 5C:
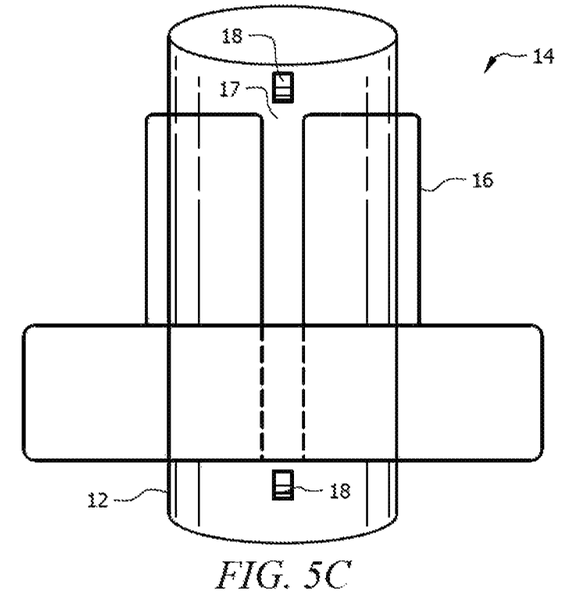
FIG. 5C is a side perspective view illustrating the retention member's ability to receive and pass projections through the projection passage.
Figure 5D:
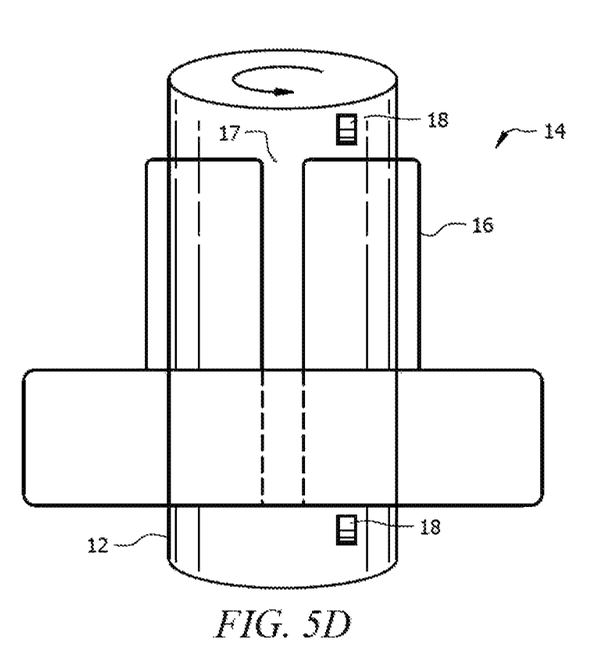
FIG. 5D is a side perspective view illustrating the rotation of the tube with respect to the retention member to bring the projection into alignment with the locking passage.
Figure 5E:
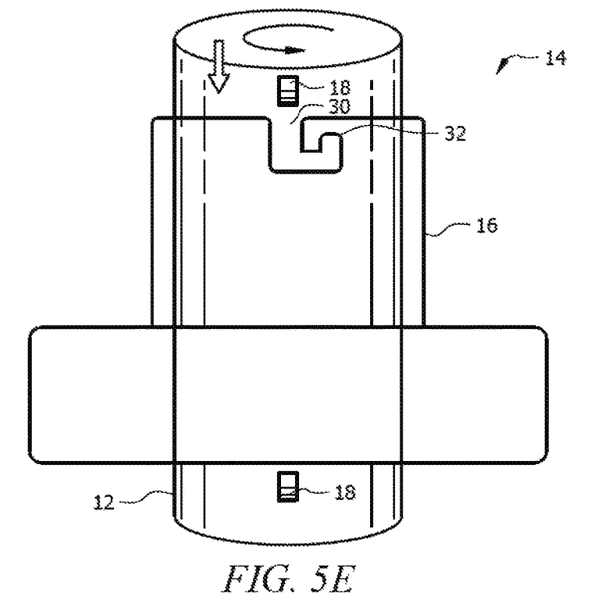
FIG. 5E is a side perspective view illustrating the alignment of the projection with the locking passage after rotating the tube with respect to the retention member.
Figure 5F:
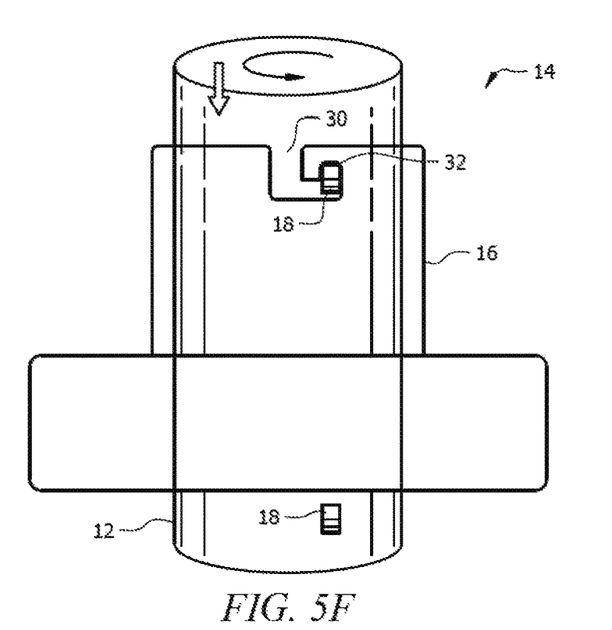
FIG. 5F is a side perspective view of the locking passage securing a projection in the securing end of the locking passage.

The L-shaped locking mechanism is designed so that at least one of projections 18 must be manually maneuvered to securing end 32 to improve the likelihood that the projection will remain in locking passage 30. As shown in FIG. 5F when in securing end 32, three sides of projection 18, or at least some portion of each of the three sides, are in contact or close proximity to securing end 32. In a certain embodiment, securing end 32 prevents projection 18 from leaving securing end 32 without first rotating then forcing retention member 14 towards the patient's body, which is unlikely to occur without purposeful human intervention. This design prevents inadvertent disengagement of securing end 32 with projection 18 and in turn prevents tube 12 from accidently further intruding into the patient's body. In a certain embodiment, the locking passage can be any shape known to a person having ordinary skill in the art such that a projection must be manually maneuvered through the locking passage to reach the securing end. Furthermore, in order to have complete dislodgement of the retention member 14, after projection 18 is unlocked from securing end 32, retention member 14 would need to be rotated until projections 18 are aligned again with passage 17, and member 14 pushed away from the patient's body, which is even less likely to occur without purposeful human intervention.

In a certain embodiment, indwelling tube 12 may be any tube, known to a person of ordinary skill in the art, that can be inserted into a body and may be made of any biocompatible material known to a person having ordinary skill in the art. Tube 12 may also contain a biocompatible coating to allow for easier translation of retention member 14 along tube 12.

In a certain embodiment, the projections are capable of varying the distance they extend from the tube. This advantage allows for a smaller incision and reduces potential trauma related to extended projections contacting the patient's surrounding skin during insertion and removal of the tube. Additionally, the tube is more easily inserted into a peel-away sheath. The distance that the projections extend from the tube can either be predetermined and fixed or possibly adjusted through pneumatic inflation. In such an embodiment, the projections may be fluidly coupled to the inflatable balloon and the balloon inflation port such that the inflatable balloon and projections inflate at generally the same time. In another embodiment, the projection may have a separate projection inflation port to allow the balloon and projections to be inflated separately. The projections may be inflatable themselves or may be generally rigid structures slidably engaged with the indwelling tube, such that the application of pneumatic pressure drives the projections from a recessed position to a raised position. The projections may have any form and/or connection to the tube as is known to a person having ordinary skill in the art, such that the projections are capable of adjusting the distance that they extend from the tube.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

GLOSSARY OF CLAIM TERMS

Distance Measuring System: is a system using incremental labeling, on the external surface of the tube.

Indwelling Medical Device: is a medical device adapted to be inserted and left within a bodily organ or passage for some period of time. Usually used to maintain drainage, prevent obstruction, or provide a route for administration of food or drugs.

Projection: is an element having a predetermined size and shape.

Retention Member: is a device to prevent inward migration of indwelling medical devices. The cross-section of the device is larger than the opening in the body.

Tube: is a tubular or hollow member.

What is claimed is:

1. An indwelling medical device comprising:
   an indwelling tube having a distal end and a proximal end, where the distal end is insertable into a living body;
   a plurality of projections longitudinally spaced along the indwelling tube at a predetermined distance from one another, wherein each projection of the plurality of projections extends a distance outwardly in a radial direction from an external surface of the indwelling tube and does not completely surround the external surface of the indwelling tube;
   a retention member comprising:
      a length extending axially, an outer perimeter, a bore disposed through the retention member in an axial direction, an inner diameter formed by the bore, and a projection passage adapted to receive the plurality of projections; and
      the bore is adapted to receive the indwelling tube, such that the indwelling tube extends past a proximal end and a distal end of the retention member;
      wherein the inner diameter formed by the bore has a magnitude less than a sum of the distance outwardly a projection of the plurality of projections extends in the radial direction and a diameter of the indwelling tube.

2. The indwelling medical device as in claim 1, wherein the retention member further includes the projection passage extending the length of the retention member, the projection passage having a size and shape such that the plurality of projections can enter and pass through the projection passage when the projection passage and the plurality of projections are aligned.

3. The indwelling medical device as in claim 2, wherein the retention member further includes a buffering extension.

4. The indwelling medical device as in claim 3, wherein the buffering extension further includes:
   a length extending in the axial direction such that a sum of the retention member's length and the buffering extension's length is less than a distance between each projection;
   the projection passage of the retention member extending a total length of the buffering extension in the axial direction of the retention member; and
   the length of the buffering extension extending towards the proximal end of the indwelling tube.

5. The indwelling medical device as in claim 1, wherein each projection of the plurality of projections is equidistantly spaced from one another.

6. The indwelling medical device as in claim 1, wherein the distance outwardly in the radial direction each projection extends is of a magnitude such that the indwelling tube is capable of sliding inside a peel-away sheath.

7. The indwelling medical device as in claim 1, further comprising a distance measuring system disposed on the indwelling tube capable of indicating an indwelling tube's depth in the living body.

8. The indwelling medical device as in claim 1, wherein the retention member further includes a locking passage directly adjacent and open to the bore, wherein the locking passage is adapted to receive the plurality of projections, the locking passage having a shape such that each projection is incapable of leaving a securing end without being forced away from the living body.

9. The indwelling medical device as in claim 1, wherein the plurality of projections are adapted to adjust in the distance outwardly in the radial direction that the plurality of projections extend from the external surface of the indwelling tube.

10. The indwelling medical device as in claim 1, further comprising an inflatable internal retention member disposed proximate to the distal end of the indwelling tube, such that the inflatable internal retention member can pass into the living body in a deflated state and then be inflated to act as an internal anchor.

11. An indwelling medical device comprising:
   an indwelling tube having a distal end and a proximal end, where the distal end is insertable into a patient's body;
   a plurality of projections longitudinally spaced along the indwelling tube at a predetermined distance from one another, wherein each projection of the plurality of projections does not completely surround an external surface of the indwelling tube;
   a retention member comprising:
      a length extending axially, an outer perimeter, a bore disposed through the retention member in an axial direction, an inner diameter formed by the bore, and a projection passage;
      the bore being adapted to receive the indwelling tube, such that the indwelling tube extends past a proximal end and a distal end of the retention member;
      the inner diameter formed by the bore has a magnitude less that a sum of a distance outwardly a projection of the plurality of projections extends and a diameter of the indwelling tube; and
      the projection passage extending the length of the retention member, the projection passage having a size and shape such that the plurality of projections can enter and pass through the projection passage when the projection passage and the plurality of projections are aligned.

12. The indwelling medical device as in claim 11, wherein the retention member further includes a buffering extension.

13. The indwelling medical device as in claim 12, wherein the buffering extension further includes:
- a length extending outwardly in the axial direction such that a sum of the retention member's length and the buffering extension's length is less than a distance between each projection;
- the projection passage of the retention member extending the total length of the buffering extension in the axial direction of the retention member; and
- the length of the buffering extension extending towards the proximal end of the indwelling tube.

14. The indwelling medical device as in claim 12, wherein the buffering extension further includes an inner diameter of the same magnitude as the inner diameter of the retention member.

15. The indwelling medical device as in claim 11, wherein each projection of the plurality of projections is equidistantly spaced from one another.

16. The indwelling medical device as in claim 11, wherein the distance outwardly in the radial direction each projection extends is of a magnitude such that the indwelling tube is capable of sliding inside a peel-away sheath.

17. The indwelling medical device as in claim 11, further comprising a distance measuring system disposed on the indwelling tube capable of indicating an indwelling tube's depth in the patient's body.

18. The indwelling medical device as in claim 11, wherein the retention member further includes an L-shaped locking passage directly adjacent and open to the bore, wherein the L-shaped locking passage is adapted to receive the plurality of projections.

19. The indwelling medical device as in claim 11, wherein the plurality of projections are adapted to adjust in the distance outwardly that the plurality of projections extend from the external surface of the indwelling tube.

* * * * *